United States Patent [19]

Tokuda et al.

[11] Patent Number: 5,175,052
[45] Date of Patent: Dec. 29, 1992

[54] ADHESIVE TAPE PREPARATION OF CLONIDINE

[75] Inventors: Shoichi Tokuda; Saburo Otsuka; Yuusuke Ito, all of Osaka, Japan

[73] Assignee: Nitto Denko Corporation, Osaka, Japan

[21] Appl. No.: 790,081

[22] Filed: Nov. 13, 1991

Related U.S. Application Data

[63] Continuation of Ser. No. 434,050, Nov. 9, 1989, abandoned.

[51] Int. Cl.⁵ .............. B32B 7/12; A61F 13/00; A61L 15/16; A61K 9/70
[52] U.S. Cl. .................. 428/355; 428/422; 428/343; 424/448; 424/449; 602/52
[58] Field of Search .......... 428/355, 343, 422; 128/156; 424/448, 449

[56] References Cited

U.S. PATENT DOCUMENTS

| | | | |
|---|---|---|---|
| 4,346,709 | 8/1982 | Schmitt | 424/449 |
| 4,592,753 | 6/1986 | Panoz | 424/449 |
| 4,608,249 | 8/1986 | Otsuka et al. | 424/28 |
| 4,765,974 | 8/1988 | Tokuda et al. | 424/443 |
| 4,822,617 | 4/1989 | Panoz | 424/449 |
| 4,994,278 | 2/1991 | Sablotsky et al. | 424/448 X |

FOREIGN PATENT DOCUMENTS 0295777 12/1988 European Pat. Off.
63-20806 4/1988 Japan.
63-21647 5/1988 Japan.

OTHER PUBLICATIONS

WPIL, File Supplier, AN=90-0040-27 (01), Derwent Publications Ltd., London, GB; & JPA 01 287 024.
Patent Abstracts of Japan, vol. 12, No. 306 (C-522)[3153], Aug. 19, 1988.

Primary Examiner—George F. Lesmes
Assistant Examiner—D. R. Zirker
Attorney, Agent, or Firm—Sughrue, Mion, Zinn, Macpeak & Seas

[57] ABSTRACT

An adhesive tape preparation of clonidine is disclosed, comprising a polytetrafluoroethylene porous sheet having an air permeability of from 10 to 500 seconds having thereon an active ingredient-containing layer comprising a pressure-sensitive adhesive obtained by copolymerizing a monomer mixture comprising from 40 to 80% by weight of 2-ethylhexyl acrylate, from 20 to 60% by weight of 2-methoxyethyl acrylate, and 0 to 40% by weight of vinyl acetate, the pressure-sensitive adhesive containing clonidine as an active ingredient. The preparation achieves sustained release of clonidine and exhibits long-term preservability while minimizing skin irritation and maintaining sufficient adhesion to the skin.

15 Claims, No Drawings

ADHESIVE TAPE PREPARATION OF CLONIDINE

This is a continuation of application Ser. No. 07/434,050, filed Nov. 9, 1989, now abandoned.

FIELD OF THE INVENTION

This invention relates to an adhesive tape preparation of clonidine and, more particularly, to an adhesive tape preparation comprising a polytetrafluoroethylene porous sheet having moderate air permeability and having thereon a layer containing clonidine as an active ingredient.

BACKGROUND OF THE INVENTION

For the purpose of extending the duration of active ingredients and reducing side effects, a percutaneous administration route which makes it feasible to strictly control doses has recently been studied as a substitution for oral administration or injection. For example, percutaneous preparations including topical preparations of antiinflammatory agents and systemic preparations of nitroglycerin, isosorbide dinitrate, scopolamine, estradiol or the like have been developed.

Also with respect to clonidine acting as a hypotensive, a percutaneous preparation of clonidine which maintains a constant level in blood over 7 days or more thus achieving a prolonged duration has been proposed in place of oral tablets containing clonidine hydrochloride as described in MacGregor, T. R., et al., *Clin. Pharmacol. Ther.*, Vol. 38(3), p. 278 (1985), U.S. Pat. No. 4,201,211, and JP-A-54-20129 (the term "JP-A" as used herein means an "unexamined published Japanese patent application").

A dose of clonidine, given orally, usually lasts for about 8 hours and therefore should be administered three times a day. This is a trouble to a patient, often causing the patient to forget to take the medicine, which may lead to serious symptoms due to a break in the effect. For this reason, attention has been called to percutaneous preparations of clonidine. Conventional percutaneous preparations of clonidine comprise a support sheet substantially impermeable to clonidine having thereon a clonidine-containing layer, a layer controlling release of clonidine, and an adhesive layer for fixing to the skin in this order.

U.S. Pat. No. 4,765,974 and JP-B-63-20806 (the term "JP-B" as used herein means an "examined published Japanese patent application") disclose percutaneous preparations comprising a support of various kinds having thereon an active ingredient-containing layer comprising a specific acrylate copolymer having dispersed therein clonidine and/or clonidine hydrochloride as an active ingredient with citric acid and/or succinic acid as a decomposition inhibitor.

JP-B-63-21647 discloses a percutaneous preparation of clonidine comprising a porous fluorine-containing resin film or sheet having a specific moisture permeability having thereon an active ingredient-containing layer.

While these conventional preparations for percutaneous administration of clonidine produce considerable effects in percutaneous absorption of clonidine, sustained clonidine release, and prevention of decomposition of clonidine during preservation (stability), no attention has been directed to suitability of the support. In particular, a support having no substantial air permeability would be of great irritation to the skin, giving rise to an extremely serious problem in practical application. JP-B-63-21647 supra suggests to use a porous fluorine-containing resin film, etc. having specific permeability to moisture as a support of low skin irritation, but sufficient study is not given to the optimum combination of components constituting the layer containing clonidine and also serving for fixing to the skin. In particular, having a hypotensive effect, clonidine must be administered under strict dose control and, therefore, adhesion to the skin is one of important subjects to consider. That is, should the preparation be partly peeled apart from the skin due to poor adhesion, migration of clonidine through the skin is reduced, failing to obtain sufficient hypotensive effect as expected.

Accordingly, in developing percutaneous preparations of an active ingredient requiring strict dose control (control on the amount percutaneously absorbed), such as clonidine, the following requirements should be satisfied. (1) The preparations must have sufficiently satisfactory adhesion to the skin. For example, peeling of even 10% of the area adhered is unacceptable. (2) The active ingredient should be stably present in the preparations, prevented from decomposition during long-term preservation. (3) In order to achieve sustained release of the active ingredient for a prolonged period of time, irritation to the skin should be minimized. For example, the skin irritation index (hereinafter defined) should not exceed 30. (4) Because clonidine is relatively expensive, it is desired to increase availability of the active ingredient. In greater detail, the rate of release to the skin surface should be at least 15%.

Under the present situation, percutaneous preparations of clonidine satisfying the above-described requirements have not yet been developed.

SUMMARY OF THE INVENTION

The inventors have conducted extensive studies to develop a percutaneous preparation of clonidine which achieves percutaneous administration of clonidine while satisfying various requirements stated above, such as adhesion to the skin and freedom from skin irritation. As a result, it has now been found that an excellent clonidine preparation is obtained by forming a active ingredient-containing layer comprising an adhesive component having a specific composition and clonidine contained therein on a polytetrafluoroethylene porous sheet having specific air permeability. The present invention has been completed based on this finding.

Other objects, effects and advantages of the present invention will be apparent from the following description.

The present invention provides an adhesive tape preparation of clonidine which comprises a polytetrafluoroethylene porous sheet having an air permeability of from 10 to 500 seconds having thereon an active ingredient-containing layer comprising a pressure-sensitive adhesive obtained by copolymerizing a monomer mixture comprising from 40 to 80% by weight of 2-ethylhexyl acrylate, from 20 to 60% by weight of 2-methoxyethyl acrylate, and from 0 to 40% by weight of vinyl acetate, the pressure-sensitive adhesive containing clonidine as an active ingredient.

When the monomer mixture comprises vinyl acetate, the active ingredient-containing layer preferably further contain succinic acid to prevent clonidine present in the adhesive tape preparation from decomposition during long-term preservation.

DETAILED DESCRIPTION OF THE INVENTION

The polytetrafluoroethylene porous sheet which can be used for supporting an active ingredient-containing layer in the present invention comprises polytetrafluoroethylene. In order to improve mechanical strength, a sintered sheet is used. The porous sheet is generally prepared by uniaxially or biaxially stretching a polytetrafluoroethylene sheet simultaneously with sintering. A number of fine pores are formed by the stretching, and porosity, pore size and air permeability of the sheet can be controlled by stretch ratio adjustment.

The polytetrafluoroethylene porous sheet used in the present invention has an air permeability of from 10 to 500 seconds, preferably from 20 to 300 seconds. If the air permeability is less than 10 seconds, such high air permeability causes strike-through of clonidine during long-[term preservation, decreasing percutaneous clonidine absorption below a practical level. If the air permeability exceeds 500 seconds, not only does skin irritation become likely, but the adhesiveness to the skin is reduced during long-term application.

The terminology "air permeability" as used herein means an average time (second) required for 100 ml of air to pass through the sheet having an area of 654 mm$^2$ as measured by means of a tester A type as specified in JIS P8117 "Testing Method of Air Permeability of Paper and Paperboard".

The porous sheet preferably has a thickness ranging from 5 to 300 μm, more preferably from 10 to 100 μm. Too thin a sheet is difficult to handle, and too thick a sheet lacks softness causing a feeling of incompatibility during application to the skin.

The active ingredient-containing layer to be used in the present invention is required to stably support clonidine, the active ingredient, and to release the active ingredient through diffusive migration while exhibiting satisfactory adhesion to the skin for a long time without irritating the skin. It was found that a pressure-sensitive adhesive obtained by copolymerizing 2-ethylhexyl acrylate, 2-methoxyethyl acrylate, and vinyl acetate is suitable as a active ingredient-containing layer satisfying the above-described requirements. As a result of further investigation, it was ascertained that a copolymer obtained from a monomer mixture comprising from 40 to 80% by weight, preferably from 40 to 70% by weight, more preferably from 45 to 60% by weight, of 2-ethylhexyl acrylate; from 20 to 60% by weight, preferably from 20 to 50% by weight, more preferably from 25 to 40% by weight, of 2-methoxyethyl acrylate; and 0 to 40% by weight, preferably from 10 to 40% by weight, more preferably from 10 to 30% by weight, of vinyl acetate is more suitable. All the percent ratios of the monomers are based on the amount of the monomer mixture.

In particular, a copolymer obtained from a monomer mixture containing more than 40% by weight of vinyl acetate has turned out to undergo reduction in adhesion to the skin and also to adversely affect clonidine release properties.

If the ratio of 2-ethylhexyl acrylate is less than 40% by weight, the active ingredient-containing layer has poor clonidine release properties. If it exceeds 80% by weight, the cohesion of the layer is so reduced that the adhesive layer remains on the skin when stripped off the skin.

If the ratio of 2-methoxyethyl acrylate is less than 20% by weight, the layer has poor clonidine release properties, and if it exceeds 60% by weight, unfavorable gelation occurs during or after the copolymerization.

The pressure-sensitive adhesive used in the present invention can be prepared by any conventional methods such as radical polymerization. The pressure-sensitive adhesive preferably has a viscosity of from 50 to 250 poise (25% by weight ethyl acetate solution at 30° C. measured by B type viscometer) and a weight average molecular weight of from 700,000 to 1,000,000 (determined by GPC).

Clonidine, an active ingredient having an action to reduce the tone of central sympathetic nervous system, is incorporated into the active ingredient-containing layer comprising the above-described pressure-sensitive adhesive preferably in an amount of from 1 to 25% by weight, more preferably from 2 to 10% by weight, based on the active ingredient-containing layer to thereby manifest hypotensive effects in the treatment or prevention of hypertension or migraine.

In the case when the pressure-sensitive adhesive contains a vinyl acetate unit, it is preferred to incorporate succinic acid into the active ingredient-containing layer to prevent decomposition of clonidine because clonidine is particularly apt to be decomposed in the presence of vinyl acetate units. In this case, succinic acid is preferably added in an amount of from 0.1 to 5% by weight, more preferably from 0.3 to 4% by weight based on the active ingredient-containing layer. Addition of less than 0.1% by weight hardly produces significant effects. Addition of more than 4% by weight brings no further improvement on prevention of clonidine decomposition and is also unfavorable from the standpoint of skin irritation and cohesion of the layer.

For the purpose of increasing the amount of clonidine to be released, the active ingredient-containing layer can further contain one or more additives, such as glycols, e.g., propylene glycol, diethylene glycol, and triethylene glycol; N-methyl-2-pyrrolidone, N-methylpyrrolidone N-oxide, salicylic acid, urea, dimethyl sulfoxide, decylmethyl sulfoxide, diethyl sebacate, ethyl alcohol, and various surface active agents. From the viewpoint of adhesion to the skin and maintenance of a cohesive force of the layer, the amount of these additives to be used is preferably not more than 20% by weight, more preferably between 0.5 and 20% by weight, based on the total weight of the active ingredient-containing layer.

The thickness of the clonidine-containing layer is preferably adjusted within a range of from 5 to 300 μm, more preferably from 10 to 100 μm, taking adhesion to the skin, cohesion, releasability from the skin, and skin irritation into consideration.

In order to effectively release clonidine to the skin while minimizing skin irritation so as to have a skin irritation index of not higher than 30, it is desirable to adjust a moisture permeability of the whole preparation to a range of from 200 to 3,000 g/m$^2$·24 hrs. With the moisture permeability below 200 g/m$^2$·24 hrs, the adhesive tape preparation applied to the skin is liable to cause stuffiness. As a result, the skin irritation becomes serious, and also the adhesion to the skin is likely to be reduced. On the other hand, if the moisture permeability exceeds 3,000 g/m$^2$·24 hrs, the effects of percutaneous administration by occlusive dressing technique (ODT) are reduced, sometimes failing to obtain sufficient pharmacological effects.

The terminology "moisture permeability" as used herein means a value obtained according to JIS Z0208 "Testing Methods for Determination of the Water Vapor Transmission Rate of Moisture-Proof Packaging Materials (Dish Method)". More specifically, the moisture permeability can be determined by placing a prescribed amount of anhydrous calcium chloride on the bottom of a moisture-permeable open top container, and the top is covered with the adhesive tape preparation of the present invention. The container is allowed to stand in a thermo-hygrostat set at a temperature of 40°±0.5° C. and at a relative humidity of 90±2% for 2 hours, and an increase of weight of the container over that before standing in the thermo-hygrostat is measured to calculate the moisture permeability per 24 hours.

The terminology "skin irritation index" as used herein means an index of primary skin irritation observed after the tape preparation of the present invention is applied to the skin of the human fore chest for 72 hours as judged according to the Draize's standard (as described in *J. Pharmacol. Exptl. Therap.*, vo.,82, pp.377-390 (1944)). Specifically, a tape preparation having an area of 0.785 cm$^2$ (10 mm in diameter) is applied to the skin of the human chest of subjects for 72 hours. The conditions of the skin, 30 minutes and 24 hours after from removing the preparation, are determined by the Draize's standard to keep the score. The above procedures are conducted twice, and using the larger score, the skin irritation index is determined by the following formula:

$$\text{skin irritation index} = \frac{\text{total score}}{\text{number of subjects}} \times 100$$

As described above, the adhesive tape preparation according to the present invention is a preparation for effectively administering clonidine through the skin. It achieves sustained release of clonidine and exhibits long-term preservability while minimizing skin irritation and maintaining sufficient adhesion to the skin. Hence, the adhesive tape preparation of the present invention produces excellent effects that have never been achieved by the conventional clonidine-containing percutaneous preparations.

The present invention is now illustrated in greater detail by way of the following Examples, but it should be understood that the present invention is not deemed to be limited thereto. Unless otherwise indicated, all the percents are given by weight in these examples.

EXAMPLE 1

In a flask, 45 g of 2-ethylhexyl acrylate, 30 g of vinyl acetate, and 25 g of 2-methoxyethyl acrylate were charged in an inert gas atmosphere. To the mixture was added 0.1 g of benzoyl peroxide as a polymerization initiator. The reaction was continued for about 10 hours under control by adjustment of the stirring speed and the external bath temperature and dropwise addition of ethyl acetate as a solvent to obtain a pressure-sensitive adhesive solution. The pressure-sensitive adhesive thus obtained had a viscosity of 130 to 160 poise at 30° C. as a 25% by weight solution and a weight average molecular weight of from 820,000 to 880,000.

Clonidine as an active ingredient and succinic acid were mixed with the resulting adhesive solution, and the composition was coated on a 60 μm thick polytetrafluoroethylene porous sheet having an air permeability of 20 seconds to a dry thickness of 50 μm to prepare an adhesive tape preparation according to the present invention. The active ingredient-containing layer had a clonidine concentration of 7.5% and a succinic acid concentration of 0.5%, and the adhesive tape preparation had a moisture permeability of 1,290 g/m$^2$·24 hrs.

EXAMPLE 2

In a flask, 60 g of 2-ethylhexyl acrylate, 20 g of vinyl acetate, and 20 g of 2-methoxyethyl acrylate were charged in an inert gas atmosphere, and 0.1 g of benzoyl peroxide as a polymerization initiator was added thereto to start polymerization. Following the same procedure as described in Example 1, a pressure-sensitive adhesive solution was obtained. The pressure-sensitive adhesive thus obtained had a viscosity of 90 to 110 poise at 30° C. as a 25% by weight solution and a weight average molecular weight of from 740,000 to 810,000.

Clonidine and succinic acid were mixed with the resulting adhesive solution, and the composition was coated on a 60 μm thick polytetrafluoroethylene porous sheet having an air permeability of 100 seconds to a dry thickness of 50 μm to prepare an adhesive tape preparation.

The active ingredient-containing layer of the resulting adhesive tape preparation had a clonidine concentration of 7.5% and a succinic acid concentration of 2%, and the adhesive tape preparation had a moisture permeability of 1,100 g/m$^2$·24 hrs.

EXAMPLE 3

Clonidine and succinic acid were mixed with the pressure-sensitive adhesive solution as obtained in Example 1, and the composition was coated on a 20 μm thick polytetrafluoroethylene porous sheet having an air permeability of 300 seconds to a dry thickness of 30 μm to prepare an adhesive tape preparation.

The active ingredient-containing layer of the adhesive tape preparation had a clonidine concentration of 10% and a succinic acid concentration of 1%, and the adhesive tape preparation had a moisture permeability of 1,540 g/m$^2$·24 hrs.

EXAMPLE 4

Clonidine and succinic acid were mixed with the pressure-sensitive adhesive solution as obtained in Example 2, and the composition was coated on a 100 μm thick polytetrafluoroethylene porous sheet having an air permeability of 200 seconds to a dry thickness of 100 μm to prepare an adhesive tape preparation.

The active ingredient-containing layer of the preparation had a clonidine concentration of 3% and a succinic acid concentration of 0.4%, and the preparation had a moisture permeability of 710 g/m$^2$·24 hrs.

EXAMPLE 5

In a flask, 75 g of 2-ethylhexyl acrylate and 25 g of 2-methoxyethyl acrylate were charged in an inert gas atmosphere, and 0.1 g of benzoyl peroxide was added thereto as a polymerization initiator to start polymerization. The same procedure as in Example 1 was followed to obtain a pressure-sensitive adhesive solution. The pressure-sensitive adhesive thus obtained had a viscosity of 80 to 100 poise at 30° C. as a 25% by weight solution and a weight average molecular weight of from 850,000 to 910,000.

Clonidine was mixed with the resulting adhesive solution, and the composition was coated on a 60 μm thick polytetrafluoroethylene porous sheet having an air permeability of 300 seconds to a dry thickness of 60 μm to obtain an adhesive tape preparation.

The active ingredient-containing layer of the resulting preparation had a clonidine concentration of 5%, and the preparation had a moisture permeability of 980 g/m·24 hrs.

EXAMPLE 6

In a flask, 55 g of 2-ethylhexyl acrylate, 15 g of vinyl acetate, and 30 g of 2-methoxyethyl acrylate were charged in an inert gas atmosphere, and 0.1 g of benzoyl peroxide as a polymerization initiator was added thereto to start polymerization. Following the same procedure as described in Example 1, a pressure-sensitive adhesive solution was obtained. The pressure-sensitive adhesive thus obtained had a viscosity of 150 to 170 poise at 30° C. as a 25% by weight solution and a weight average molecular weight of from 880,000 to 950,000.

Clonidine was mixed with the resulting adhesive solution, and the composition was coated on a 60 μm thick polytetrafluoroethylene porous sheet having an air permeability of 20 seconds to a dry thickness of 50 μm to prepare an adhesive tape preparation.

The active ingredient-containing layer of the resulting adhesive tape preparation had a clonidine concentration of 7.5%, and the adhesive tape preparation had a moisture permeability of 1,310 g/m$^2$·24 hrs.

COMPARATIVE EXAMPLE 1

An adhesive tape preparation was obtained in the same manner as in Example 1, except for replacing the polytetrafluoroethylene porous sheet with a 9 μm thick air-impermeable polyester film. The resulting adhesive tape preparation had a moisture permeability of 15 g/m$^2$·24 hrs.

COMPARATIVE EXAMPLE 2

An adhesive tape preparation was obtained in the same manner as in Example 2, except for replacing the polytetrafluoroethylene porous sheet with a 80 μm thick polyethylene porous sheet having an air permeability of 200 seconds. The resulting adhesive tape preparation had a moisture permeability of 1,000 g/m$^2$·24 hrs.

COMPARATIVE EXAMPLE 3

An adhesive tape preparation was obtained in the same manner as in Example 2, except for replacing the polytetrafluoroethylene porous sheet with a 60 μm thick polytetrafluoroethylene sheet which was substantially impermeable to air (air permeability: 36,000 seconds or more). The resulting adhesive tape preparation had a moisture permeability of 13 g/m$^2$·24 hrs.

COMPARATIVE EXAMPLE 4

An adhesive tape preparation was obtained in the same manner as in Example 1, except for replacing the polytetrafluoroethylene porous sheet with a 60 μm thick polytetrafluoroethylene sheet having an air permeability of 5 second. The resulting adhesive tape preparation had a moisture permeability of 2,380 g/m$^2$·24 hrs.

COMPARATIVE EXAMPLE 5

An adhesive tape preparation was obtained in the same manner as in Example 1, except for replacing the polytetrafluoroethylene porous sheet with a 60 μm thick polytetrafluoroethylene sheet having an air permeability of 700 second. The resulting adhesive tape preparation had a moisture permeability of 150 g/m$^2$·24 hrs.

Primary skin irritation, adhesion to the skin, migration of clonidine to the skin, and clonidine preservation stability of each of the adhesive tape preparations obtained in Examples 1 to 6 and Comparative Examples 1 to 5 were evaluated according to the following test methods, and the results obtained are shown in Table 1 below.

1) Primary Skin Irritation

A tape preparation having an area of 0.785 cm$^2$ (10 mm in diameter) was applied to the skin of the human chest of subjects for 72 hours. The conditions of the skin, 30 minutes and 24 hours after from removing the preparation, were determined by the Draize's standard to determine the total score. The above procedures were conducted twice, and using the larger score, the sking irritation index was determined by the following formula:

$$\text{skin irritation index} = \frac{\text{total score}}{\text{number of subjects}} \times 100$$

2) Adhesion to the Skin

The preparation sample was applied to the skin of the human fore chest for 72 hours, and the rate of adhesion (%) was calculated from the area adhered immediately after the application and that after the 72 hours application.

3) Rate of Migration to the Skin

The preparation sample was applied to the shaved back of a rabbit for 24 hours. The concentration of residual clonidine in the preparation was measured to obtain a rate of migration to the skin (%).

4) Preservation Stability

The preparation sample was preserved at 40° C. for 1 year, and the concentration of residual clonidine in the preparation was measured to obtain a clonidine retention (%).

TABLE 1

| Example No. | Skin irritation index | Rate of adhesion (%) | Rate of clonidine migration (%) | Rate of clonidine retention (%) |
| --- | --- | --- | --- | --- |
| Example 1 | 5 | 99.4 | 21 | 99.8 |
| Example 2 | 9 | 99.2 | 27 | 99.7 |
| Example 3 | 12 | 98.5 | 33 | 99.9 |
| Example 4 | 15 | 99.0 | 28 | 99.7 |
| Example 5 | 12 | 98.7 | 27 | 98.7 |
| Example 6 | 8 | 99.0 | 31 | 96.5 |
| Comparative Example 1 | 42 | 54.2 | 57 | 99.8 |
| Comparative Example 2 | 10 | 99.4 | 28 | 90.3 |
| Comparative Example 3 | 48 | 53.7 | 52 | 99.5 |
| Comparative Example 4 | 6 | 99.4 | 12 | 93.4 |
| Comparative Example 5 | 32 | 90.0 | 40 | 99.5 |

It is understood from the results in Table 1 above that the adhesive tape preparations according to the present invention are excellent in adhesion property to the skin, stability of the active ingredient in the preparations, sustained release of the active ingredient, and availability of the active ingredient.

While the invention has been described in detail and with reference to specific embodiments thereof, it will be apparent to one skilled in the art that various changes and modifications can be made therein without departing from the spirit and scope thereof.

What is claimed is:

1. An adhesive tape preparation of clonidine which comprises a polytetrafluoroethylene porous backing having an air permeability of from 10 to 500 seconds having thereon an active ingredient-containing layer comprising a pressure-sensitive adhesive obtained by copolymerizing a monomer mixture comprising from 40 to 80% by weight of 2-ethylhexyl acrylate, from 20 to 60% by weight of 2-methoxyethyl acrylate, and 10 to 40% by weight of vinyl acetate, said pressure-sensitive adhesive containing clonidine as an active ingredient in a concentration of from 1 to 25% by weight based on the active ingredient-containing layer; said preparation having a moisture permeability of from 200 to 3000 g/m² per 24 hours and a skin irritation index of less than 30.

2. An adhesive tape preparation as claimed in claim 1, wherein the polytetrafluoroethylene porous backing has a thickness of from 5 to 300 μm.

3. An adhesive tape preparation as claimed in claim 1, wherein the polytetrafluoroethylene porous backing has an air permeability of from 20 to 300 seconds.

4. An adhesive tape preparation as claimed in claim 1, wherein said active ingredient-containing layer has a thickness of from 5 to 300 μm.

5. An adhesive tape preparation as claimed in claim 1, wherein said active ingredient-containing layer further contains succinic acid.

6. An adhesive tape preparation as claimed in claim 5, wherein said succinic acid is present in a concentration of from 0.1 to 5% by weight based on the active ingredient-containing layer.

7. An adhesive tape preparation as claimed in claim 1, wherein said active ingredient-containing layer comprises a pressure-sensitive adhesive obtained by copolymerizing a monomer mixture comprising from 40 to 70% by weight of 2-ethylhexyl acrylate, from 20 to 50% by weight of 2-methoxyethyl acrylate, and 10 to 40% by weight of vinyl acetate.

8. An adhesive tape preparation as claimed in claim 7, wherein said preparation has a moisture permeability of from 200 to 3,000 g/m·24 hrs.

9. An adhesive tape preparation as claimed in claim 7, wherein the polytetrafluoroethylene porous backing has a thickness of from 5 to 300 μm.

10. An adhesive tape preparation as claimed in claim 7, wherein said polytetrafluoroethylene porous backing has an air permeability of from 20 to 300 seconds.

11. An adhesive tape preparation as claimed in claim 7, wherein clonidine is present in a concentration of from 1 to 25% by weight based on the active ingredient-containing layer.

12. An adhesive tape preparation as claimed in claim 7, wherein said active ingredient-containing layer has a thickness of from 5 to 300 μm.

13. An adhesive tape preparation as claimed in claim 7, wherein said active ingredient-containing layer further contains succinic acid.

14. An adhesive tape preparation as claimed in claim 13, wherein said succinic acid is present in a concentration of from 0.1 to 5% by weight based on the active ingredient-containing layer.

15. An adhesive tape preparation as claimed in claim 7, wherein said preparation has a skin irritation index of not more than 30.

* * * * *